US012752050B2

(12) United States Patent
Latouche et al.

(10) Patent No.: US 12,752,050 B2
(45) Date of Patent: Oct. 6, 2026

(54) INFUSION PUMP

(71) Applicant: INSULET CORPORATION, Acton, MA (US)

(72) Inventors: Eduardo Luis Latouche, Chelsea, MA (US); John Richard Bussiere, Littleton, MA (US); Zhifei Ge, Cambridge, MA (US)

(73) Assignee: INSULET CORPORATION, Acton, MA (US)

( * ) Notice: Subject to any disclaimer, the term of this patent is extended or adjusted under 35 U.S.C. 154(b) by 786 days.

(21) Appl. No.: 18/014,861

(22) PCT Filed: Jul. 6, 2021

(86) PCT No.: PCT/US2021/040447

§ 371 (c)(1),
(2) Date: Jan. 6, 2023

(87) PCT Pub. No.: WO2022/010849

PCT Pub. Date: Jan. 13, 2022

(65) Prior Publication Data

US 2023/0285661 A1 Sep. 14, 2023

Related U.S. Application Data

(60) Provisional application No. 63/048,969, filed on Jul. 7, 2020.

(51) Int. Cl.

| | |
|---|---|
| ***A61M 5/142*** | (2006.01) |
| ***A61M 5/14*** | (2006.01) |
| ***A61M 5/168*** | (2006.01) |

(52) U.S. Cl.

CPC ...... *A61M 5/14212* (2013.01); *A61M 5/1409* (2013.01); *A61M 5/16804* (2013.01); *A61M 2205/18* (2013.01); *A61M 2205/3331* (2013.01)

(58) Field of Classification Search

CPC ............ A61M 5/14212; A61M 5/1409; A61M 5/16804; A61M 2205/18;

(Continued)

(56) References Cited

U.S. PATENT DOCUMENTS

| | | | |
|---|---|---|---|
| 4,522,622 | A | 6/1985 | Peery et al. |
| 5,848,991 | A | 12/1998 | Gross et al. |

(Continued)

FOREIGN PATENT DOCUMENTS

| | | | |
|---|---|---|---|
| DE | 102008026696 | A1 | 6/2010 |
| EP | 0 791 369 | A1 | 8/1997 |

OTHER PUBLICATIONS

Invitation to Pay Additional Fees for International Application No. PCT/US2021/040447 dated Oct. 6, 2021.

(Continued)

*Primary Examiner* — Philip E Stimpert
(74) *Attorney, Agent, or Firm* — Goodwin Procter LLP

(57) ABSTRACT

Infusion pumps including a plurality of reservoirs arranged either serially and/or in parallel with one another are described. In some embodiments, flow channels with a desired arrangement of flow resistances, bypass flow paths, pressure sensors, and/or meniscus control structures may be included in the infusion pump to provide a desired flow of one or more therapeutic compounds into and/or out from an infusion pump.

20 Claims, 13 Drawing Sheets

(58) Field of Classification Search
CPC ....... A61M 2205/3331; A61M 5/14224; F04B 19/006; F04B 23/04; F04B 43/043
USPC ........................................................ 604/151
See application file for complete search history.

(56) References Cited

U.S. PATENT DOCUMENTS

| | | | | |
|---|---|---|---|---|
| 6,699,218 | B2 | 3/2004 | Flaherty et al. | |
| 2003/0216684 | A1* | 11/2003 | Fentress ................ | A61M 5/148 604/81 |
| 2007/0156086 | A1 | 7/2007 | Fentress et al. | |
| 2009/0056822 | A1 | 3/2009 | Young et al. | |
| 2012/0273077 | A1 | 11/2012 | Lang et al. | |
| 2014/0134002 | A1* | 5/2014 | Brettschneider .... | B01L 3/50273 417/389 |
| 2015/0025461 | A1 | 1/2015 | Corso et al. | |
| 2017/0121659 | A1 | 5/2017 | Hinojosa et al. | |
| 2019/0091417 | A1 | 3/2019 | McCaffrey et al. | |

OTHER PUBLICATIONS

International Search Report and Written Opinion for International Application No. PCT/US2021/040447 dated Dec. 21, 2021.
International Preliminary Report on Patentability (Chapter 1) for International Application No. PCT/US2021/040447 dated Jan. 19, 2023.
EP 21837364.5, Jun. 24, 2024, Extended European Search Report.
Extended European Search Report for EP Application No. 21837364.5 dated Jun. 24, 2024.

* cited by examiner

INFUSION PUMP

CROSS REFERENCE TO RELATED APPLICATION

This application is a national stage filing under 35 U.S.C. § 371 of International Patent Application Serial No. PCT/US2021/040447, filed Jul. 6, 2021 which claims priority to U.S. Provisional Application Ser. No. 63/048,969, filed Jul. 7, 2020, the entire contents of each of which are incorporated herein by reference in their entirety.

FIELD

Disclosed embodiments are related to infusion pumps and their methods of operation.

BACKGROUND

Ambulatory infusion pumps are oftentimes used for delivering a desired composition, such as a therapeutic compound, to a subject over long-duration periods. Depending on the particular application, ambulatory infusion pumps may either be used to deliver the desired composition subcutaneously, epidurally, and/or intravenously. Ambulatory infusion pumps are typically used for delivering these compositions to subjects where either continuous and/or repeated infusions of the composition are desired for a particular treatment. For example, certain conditions such as diabetes, cancer, chronic pain, infections, gastrointestinal conditions and others may benefit from treatments using ambulatory infusion pumps.

SUMMARY

In one aspect, infusion pumps are provided. In some embodiments, the infusion pump includes a plurality of serially connected reservoirs. A flow resistance between adjacent reservoirs of the plurality of serially connected reservoirs increases in a downstream direction. Infusion pump also includes an outlet, and a last downstream reservoir of the plurality of serially connected reservoirs is fluidly connected to the outlet.

In another aspect, infusion pumps are provided. In some embodiments, the infusion pump includes a first reservoir, a second reservoir, a third reservoir, an outlet of the infusion pump, a first channel extending between the first reservoir and the second reservoir, a second channel extending between the second reservoir and the third reservoir, and a third channel extending between the third reservoir and the outlet of the infusion pump. A flow resistance of the third channel is greater than a flow resistance of the second channel, and the flow resistance of the second channel is greater than a flow resistance of the first channel.

In yet another aspect, methods are provided. In some embodiments, the method of operating an infusion pump includes flowing a liquid from a first reservoir to a second reservoir through a first channel having a first flow resistance, and flowing the liquid from the second reservoir to an outlet of the infusion pump through a second channel having a second flow resistance greater than the first flow resistance.

In yet another aspect, infusion pumps are provided. In some embodiments, the infusion pump includes a first reservoir, a second reservoir, a chamber, and an outlet of the infusion pump. The first and second reservoirs are fluidly connected to the chamber in parallel, and the outlet of the infusion pump is fluidly connected to the chamber.

In yet another aspect, infusion pumps are provided. In some embodiments, the infusion pump includes a first plurality of serially connected reservoirs, a second plurality of serially connected reservoirs, a chamber, and an outlet of the infusion pump. The first and second pluralities of serially connected reservoirs are fluidly connected to the chamber in parallel, and the outlet of the infusion pump is fluidly connected to the chamber.

In yet another aspect, methods are provided. In some embodiments, the method of operating an infusion pump, the method includes flowing a first liquid from a first reservoir to a chamber, flowing a second liquid from a second reservoir to the chamber in parallel with the first liquid, mixing the first and second liquids, and flowing the mixture of the first and second liquids through an outlet of the infusion pump.

In yet another aspect, infusion pumps are provided. In some embodiments, the infusion pump includes a first reservoir, a second reservoir, a primary channel fluidly coupling the first reservoir to the second reservoir, and a bypass channel fluidly coupling the first reservoir to the second reservoir. The bypass channel is separate from at least a portion of the primary channel, and the bypass channel is configured such that a liquid is prevented from flowing through the bypass channel below a pressure threshold and the liquid is permitted to flow through the bypass channel above the pressure threshold.

In yet another aspect, methods are provided. In some embodiments, the method of operating an infusion pump includes flowing a liquid between a first reservoir and a second reservoir through a primary channel at a first pressure below a pressure threshold, and flowing the liquid between the first reservoir and the second reservoir at a second pressure greater than the pressure threshold, where at least a portion of the liquid bypasses at least a portion of the primary channel as the liquid flows between the first reservoir and the second reservoir at the second pressure.

In yet another aspect, infusion pumps are provided. In some embodiments, the infusion pump includes a first elongated reservoir, a first inlet disposed on an upstream portion of the first elongated reservoir, and a first outlet disposed on a downstream portion of the first elongated reservoir. The first elongated reservoir is sized and shaped such that a liquid flowing through the first inlet into the first elongated reservoir forms a first meniscus where the first outlet is offset in a transverse direction from a longitudinal axis of the first elongated reservoir. The downstream portion of the first elongated reservoir adjacent to the first outlet is configured to guide a portion of the first meniscus disposed on the opposing side of the longitudinal axis towards the first outlet.

In yet another aspect, methods are provided. In some embodiments, the method of operating an infusion pump includes flowing a liquid through a first inlet of a first reservoir to form a first meniscus across a width of the first reservoir, displacing the first meniscus along a length of the first reservoir as the liquid fills the first reservoir, and reducing a profile of the meniscus to guide the first meniscus towards a first outlet of the first reservoir.

In yet another aspect, infusion pumps are provided. In some embodiments, the infusion pump includes a reservoir extending from an upstream portion of the reservoir to a downstream portion of the reservoir, and the reservoir includes a first interior surface disposed on a first side of a longitudinal axis of the reservoir and a second interior surface disposed on a second side of the longitudinal axis opposite the first side. Infusion pump also includes an inlet formed in the upstream portion of the reservoir and an outlet formed in the downstream portion of the reservoir on the second side of the longitudinal axis. A curvature of the first interior surface proximate to the outlet is greater than a curvature of the second interior surface proximate to the outlet.

In yet another aspect, infusion pumps are provided. In some embodiments, the infusion pump includes a plurality of serially connected elongated reservoirs. Each elongated reservoir includes an inlet disposed on an upstream portion of the elongated reservoir and an outlet disposed on a downstream portion of the elongated reservoir where the elongated reservoir is sized and shaped such that a liquid flowing through the inlet forms a meniscus with the outlet offset in a transverse direction from a longitudinal axis of the elongated reservoir. The downstream portion of each elongated reservoir is adjacent to the outlet is configured to guide a portion of the meniscus disposed on the opposing side of the longitudinal axis towards the outlet. Additionally, the inlets and outlets of the plurality of elongated reservoirs are fluidly connected in series.

In yet another aspect, infusion pumps are provided. In some embodiments, the infusion pump includes at least one reservoir, a chamber fluidly connected to the at least one reservoir, an outlet of the infusion pump fluidly connected to the chamber, a sensor configured to sense a pressure in the chamber, at least one pump operatively coupled to the at least one reservoir and configured to pump a liquid from the at least one reservoir to the chamber and through the outlet of the infusion pump, and a processor operatively coupled to the sensor and the at least one pump. The processor is configured to control operation of the at least one pump based at least partly on the sensed pressure in the chamber.

In yet another aspect, methods are provided. In some embodiments, the method of operating an infusion pump includes flowing liquid from at least one reservoir through a chamber to an outlet of the infusion pump, sensing a pressure in the chamber, and controlling the flow of liquid from the at least one reservoir based at least partly on the sensed pressure in the chamber.

In yet another aspect, infusion pumps are provided. In some embodiments, the infusion pump includes at least one reservoir, a chamber, at least one channel that fluidly connects the at least one reservoir to the chamber, an outlet channel, an outlet of the infusion pump, and a pressure sensor configured to sense a pressure within the chamber. The outlet channel fluidly connects the chamber to the outlet of the infusion pump, and a maximum transverse dimension of the chamber is larger than a maximum transverse dimension of the at least one channel and the outlet channel.

In any of the embodiments above, an infusion pump includes a plurality of channels. In some embodiments, each reservoir upstream from the last downstream reservoir is connected to an adjacent downstream reservoir of the serially connected reservoirs by at least one channel of the plurality of channels. In some embodiments, the plurality of channels are configured to provide the increasing flow resistance between adjacent reservoirs in the downstream direction.

In any of the embodiments above, an infusion pump includes an outlet channel fluidly connected to the last downstream reservoir and the outlet of the infusion pump.

In any of the embodiments above, an infusion pump includes at least one therapeutic compound disposed in the reservoirs.

In any of the embodiments above, an infusion pump includes at least one pump operatively coupled to at least one of the reservoirs. In some embodiments, the at least one pump includes a plurality of pumps. In some embodiments, Each pump is operatively coupled with a separate reservoir of the plurality of serially connected reservoirs.

In any of the embodiments above, an infusion pump includes a filling port fluidly connected to the first reservoir/a first upstream reservoir of the plurality of serially connected reservoirs.

In any of the embodiments above, flowing the liquid from the second reservoir includes flowing the liquid from the second reservoir to a third reservoir through the second channel and flowing the liquid from the third reservoir to the outlet of the infusion pump.

In any of the embodiments above, flowing the liquid from the third reservoir to the outlet includes flowing the liquid through a third channel having a third flow resistance greater than the second flow resistance.

In any of the embodiments above, the method includes filling the first and second reservoirs through a filling port fluidly connected to the first reservoir.

In any of the embodiments above, each channel of the plurality of channels has an average maximum transverse dimension that is smaller than an average maximum transverse dimension of upstream channels of the plurality of channels.

In any of the embodiments above, a flow resistance between the last downstream reservoir and the outlet is greater than a flow resistance between the last downstream reservoir and an adjacent upstream reservoir of the plurality of reservoirs.

In any of the embodiments above, a maximum transverse dimension of each channel of the plurality of channels is between or equal to 0.1 mm and 1 mm.

In any of the embodiments above, an infusion pump includes a first pump operatively coupled to the first reservoir and a second pump operatively coupled to the second reservoir.

In any of the embodiments above, an infusion pump includes a processor operatively coupled to the first pump and the second pump. In some embodiments, the processor is configured to operate the first pump to provide a first flow rate, and the processor is configured to operate the second pump to provide a second flow rate different from the first flow rate.

In any of the embodiments above, an infusion pump includes a first therapeutic compound disposed in the first reservoir and a second therapeutic compound disposed in the second reservoir.

In any of the embodiments above, an infusion pump includes a first set of one or more pumps operatively coupled to the first plurality of serially connected reservoirs and a second set of one or more pumps operatively coupled to the second plurality of serially connected reservoirs.

In any of the embodiments above, the pumps are configured to be controlled independently.

In any of the embodiments above, an infusion pump includes a first therapeutic compound disposed in the first plurality of serially connected reservoirs and a second therapeutic compound disposed in the second plurality of serially connected reservoirs.

In any of the embodiments above, the flow of the first liquid has a first flow rate and the flow of the second liquid has a second flow rate different from the first flow rate.

In any of the embodiments above, the first liquid includes a first therapeutic compound and the second liquid includes a second therapeutic compound.

In any of the embodiments above, an infusion pump includes an outlet of the infusion pump. In some embodiments, the second reservoir is fluidly coupled to the outlet of the infusion pump.

In any of the embodiments above, the liquid has a surface tension and the bypass channel has a maximum transverse dimension at an opening into the first reservoir. In some embodiments, the surface tension and maximum transverse dimension are configured to prevent flow of the liquid through the bypass channel below the pressure threshold.

In any of the embodiments above, the bypass channel is completely separate from the primary channel.

In any of the embodiments above, the bypass channel extends between a first upstream portion of the primary channel and a second downstream portion of the primary channel.

In any of the embodiments above, an average transverse dimension of the bypass channel is less than an average transverse dimension of the primary channel.

In any of the embodiments above, the average transverse dimension of the bypass channel is between 0.05 mm and 0.5 mm.

In any of the embodiments above, the average transverse dimension of the primary channel is between 0.1 mm and 2 mm.

In any of the embodiments above, an infusion pump includes at least one therapeutic compound disposed in the first reservoir and the second reservoir.

In any of the embodiments above, an infusion pump includes at least one pump operatively coupled to the first and second reservoirs.

In any of the embodiments above, the at least one pump includes a first pump operatively coupled to the first reservoir and a second pump operatively coupled to the second reservoir.

In any of the embodiments above, an infusion pump includes a filling port fluidly connected to the first reservoir.

In any of the embodiments above, a method includes exceeding a surface tension of the liquid to flow the liquid through a bypass channel to bypass the primary channel.

In any of the embodiments above, a method includes filling the first and second reservoirs through a filling port fluidly connected to the first reservoir.

In any of the embodiments above, an axis passing through the inlet is substantially parallel to the longitudinal axis of the reservoir.

In any of the embodiments above, an axis passing through the outlet is substantially parallel to the longitudinal axis of the reservoir.

In any of the embodiments above, the inlet is formed in an upstream portion of the reservoir. In some embodiments, the outlet is formed in a downstream portion of the reservoir on a second side of the longitudinal axis opposite the first side.

In any of the embodiments above, the reservoir includes a first interior surface disposed on the first side of the longitudinal axis and a second interior surface disposed on the second side of the longitudinal axis opposite the first side. In some embodiments, a curvature of the first interior surface proximate to the outlet is greater than a curvature of the second interior surface proximate to the outlet.

In any of the embodiments above, a width of the reservoir tapers towards the outlet to guide the portion of the meniscus to the reservoir outlet In any of the embodiments above, a length of the reservoir parallel to the longitudinal axis of the reservoir is between or equal to 10 mm and 40 mm.

In any of the embodiments above, a maximum transverse dimension of the reservoir perpendicular to the longitudinal axis of the reservoir is between or equal to 5 mm and 15 mm.

In any of the embodiments above, a ratio of a radius of curvature of the first interior surface and a radius of curvature of the second interior surface proximate to the outlet is between or equal to 1 mm and 8 mm.

In any of the embodiments above, the reservoir is asymmetric.

In any of the embodiments above, an infusion pump includes at least one pump includes at least two pumps separately associated with the at least two reservoirs. In some embodiments, the processor is configured to operate the at least two pumps independently based at least partly on the sensed pressure in the chamber.

In any of the embodiments above, a sensing area of the pressure sensor is larger than the maximum transverse dimension of the at least one channel and the outlet channel.

In any of the embodiments above, the at least one reservoir includes at least two reservoirs connected to the chamber in parallel.

In any of the embodiments above, the at least two reservoirs contain different therapeutic compounds.

In any of the embodiments above, an infusion pump includes at least one pump operatively coupled to the at least one reservoir and configured to pump a liquid from the at least one reservoir to the chamber and through the outlet of the infusion pump, and a processor operatively coupled to the sensor and the at least one pump. In some embodiments, the processor is configured to control operation of the at least one pump based at least partly on the sensed pressure in the chamber.

In any of the embodiments above, the processor is configured to stop operation of the at least one pump when a detected pressure is greater than a threshold pressure.

In any of the embodiments above, the processor is configured to output an alarm when a sensed pressure rise is less than a predetermined pressure rise.

In any of the embodiments above, the at least one pump includes an electrochemical cell configured to generate a gas to displace the liquid in the at least one reservoir. In some embodiments, the processor is configured to control operation of the electrochemical cell based at least partly on the sensed pressure in the chamber.

In any of the embodiments above, a method includes stopping the flow of liquid when a detected pressure is greater than a threshold pressure.

In any of the embodiments above, a method includes determining that a sensed pressure rise is less than a predetermined pressure rise, and outputting an alarm when the sensed pressure rise is less than the predetermined pressure rise.

In any of the embodiments above, controlling the flow of liquid from the at least one reservoir includes controlling operation of an electrochemical cell to generate a gas to displace the liquid in the at least one reservoir based at least partly on the sensed pressure in the chamber.

In any of the embodiments above, flowing liquid from the at least one reservoir includes flowing parallel flows of liquid from at least two reservoirs to the chamber.

In any of the embodiments above, a method includes independently controlling the parallel flows from the at least two reservoirs based at least partly on the sensed pressure in the chamber.

In any of the embodiments above, the at least two reservoirs contain different therapeutic compounds.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
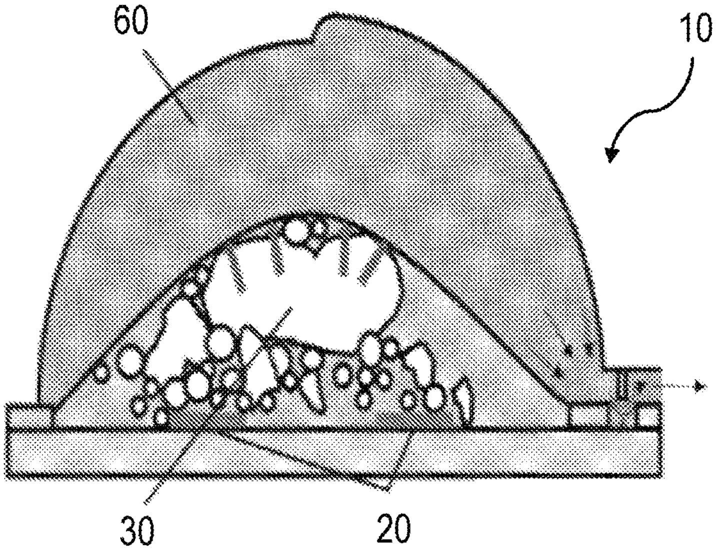
FIG. 1 is a schematic cross-sectional view of one embodiment of an electrochemical actuator.

To provide a desired delivery rate of a substance by an infusion pump, infusion pumps oftentimes include expensive and/or bulky pumps. These pumps may both increase the size and limit the amount of a therapeutic compound that may be provided to a subject within a desired form factor. Accordingly, the Inventors have recognized a need for pumps that are smaller in form factor, easier to manufacture, offer modular volume capabilities, and/or that provide improved accuracy relative to current infusion pumps.

In view of the above, the Inventors have recognized the benefits associated with infusion pumps including multiple reservoirs associated with one or more pumps, such as electrochemical actuators. Depending on the particular embodiment, the multiple reservoirs may either be arranged serially with one another and/or in parallel. For example, in one embodiment, an infusion pump may include a plurality of serially connected reservoirs which may or may not be located in parallel with one or more other sets of serially connected reservoirs. Alternatively, in some embodiments, a plurality of reservoirs of an infusion pump may be located in parallel with one another. In some instances, it may be desirable to increase a flow resistance between adjacent reservoirs such that the flow resistance along a given flow path increases in the downstream direction. Especially when used with multiple flow paths that are located in parallel with one another, such an arrangement may help to equalize filling rates of the flow paths during a filling procedure.

In addition to the above, in some embodiments, other hydraulic components and features may also be included in an infusion pump. For example, in some embodiments, an infusion pump may include bypass channels extending between adjacent reservoirs that permit at least a portion of a flow of liquid between adjacent reservoirs to flow through the bypass channels to reduce a flow rate of liquid through one or more primary channels extending between the reservoirs above a predetermined threshold pressure. The reservoirs may also be configured to control the formation and velocity profile of a meniscus during a filling procedure to help guide the meniscus towards an outlet of each reservoir to help reduce the formation of bubbles during a filling procedure.

The use of various combinations of the above methods and components, as well as other methods and components described herein, may help to provide a robust infusion pump capable of being easily manufactured and operated.

For the sake of clarity, single primary channels and bypass channels extending between adjacent reservoirs have been depicted in the figures. However, it should be understood that the various embodiments described herein may include either single or multiple primary channels and bypass channels extending between adjacent reservoirs as the disclosure is not limited in this fashion. Additionally, in embodiments where multiple bypass channels extend between adjacent reservoirs, the multiple bypass channels may either have the same threshold pressure and/or different thresholds pressures above which a liquid may flow through the bypass channels to a downstream reservoir as the disclosure is not limited in this fashion.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 presents a schematic of one embodiment of how gas electrolysis may be used to operate an electrochemical actuator 10 as described herein. Specifically, electrodes 20 disposed within an electrolytic chamber 30 apply a voltage differential to an electrolyte disposed within the electrolytic chamber to disassociate the electrolyte into a gas. The evolved gas produces a pressure for driving the flow of therapeutic compound, or other appropriate composition, from the actuator. The reservoir containing the therapeutic compounds, or other composition, and the electrolytic chamber are separated by a flexible membrane 60, so that the electrolyte is not mixed with the medication. The flexible membrane may exhibit the desired mechanical flexibility and barrier properties for the particular application for which it is used. The amount of the therapeutic compound displaced out of the reservoir may be determined by the amount of gas generated within the actuator. The amount of generated gas is determined by the total charge passed through the two electrodes which can be measured using an appropriate current sensor, Coulomb counting sensor, or other appropriate type of sensor.

Figure 2:
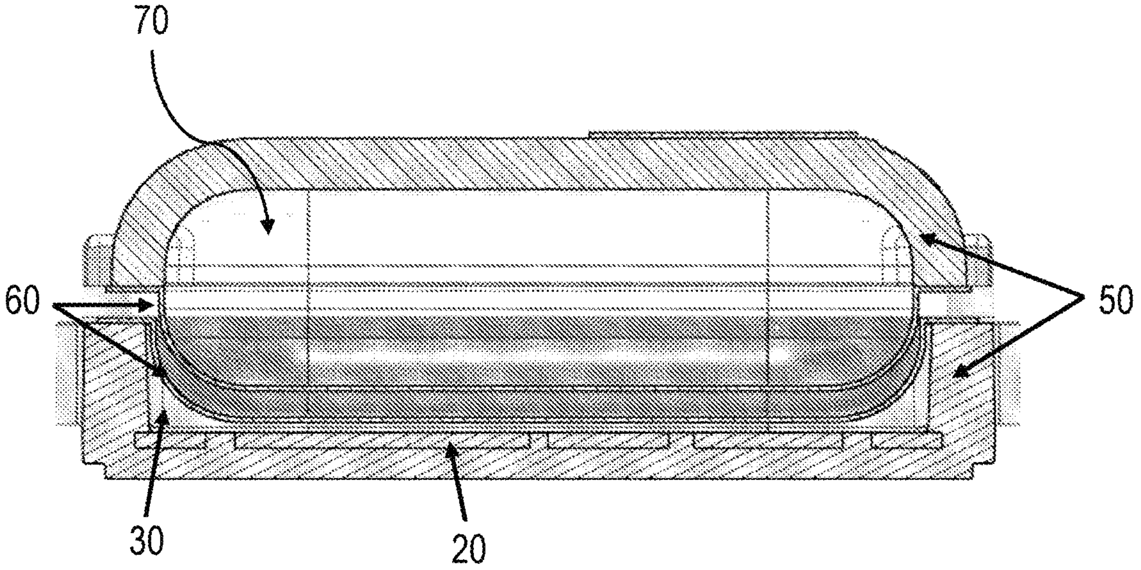
FIG. 2 is a schematic cross-sectional view of one embodiment of an electrochemical actuator.

FIG. 2 depicts another embodiment of an electrochemical actuator. In the depicted embodiment, the electrochemical actuator includes a sealed chamber formed in a rigid structure 50 in the form of an electrolytic chamber 30 including a bottom portion and one or more side portions extending from the bottom portion. In some embodiments, the rigid structure 50 is a unitary structure that is formed as a single integral component. A compliant membrane 60 is sealed around an opening formed by the one or more side portions to form the sealed electrolytic chamber 30 containing an electrolyte. Two or more electrodes 20 may extend into the interior of the sealed chamber through either a side and/or bottom portion of the rigid structure forming the chamber. The electrodes 20 may be sealed to the rigid structure in any appropriate fashion to ensure that the chamber is sealed. A second compliant membrane is sealed to a separate rigid structure such as a rigid membrane or other structure to form a reservoir 70 containing a desired therapeutic compound or other substance there between. The resulting reservoir 70 is then placed into the opening of the rigid structure with the second compliant membrane of the reservoir disposed on the first compliant membrane of the electrolytic chamber. The reservoir 70 may be held against the electrolytic chamber in any appropriate fashion including, for example, bonding, welding, and/or clamping the reservoir within the opening against the first flexible membrane of the electrolytic chamber 30. Thus, the first membrane of the electrolytic chamber may be deformed against the second membrane of the reservoir by gas generated within the electrolytic chamber 30 to displace a liquid from within the reservoir 70 through an outlet of the reservoir.

In the above embodiment, the first compliant membrane is used to contain an electrolyte to be used to electrolysis within the electrolytic chamber 30 and the second compliant membrane is in contact with a liquid therapeutic compound, or other substance, contained within the reservoir 70 after filling. Advantageously, the reservoir 70 may go through an independent fabrication process to that of the electrolytic chamber 30. This approach may offer several advantages in isolating the therapeutic compounds, or other substance, from potential interaction with the electrolyte used for electrolysis. It may also facilitate quality control steps of the two items. Considering the technical requirements for therapeutic compounds packaging and electrolyte containment, this manufacturing approach may also increase the number of options available for materials to be used in the construction of these components.

Figure 3:
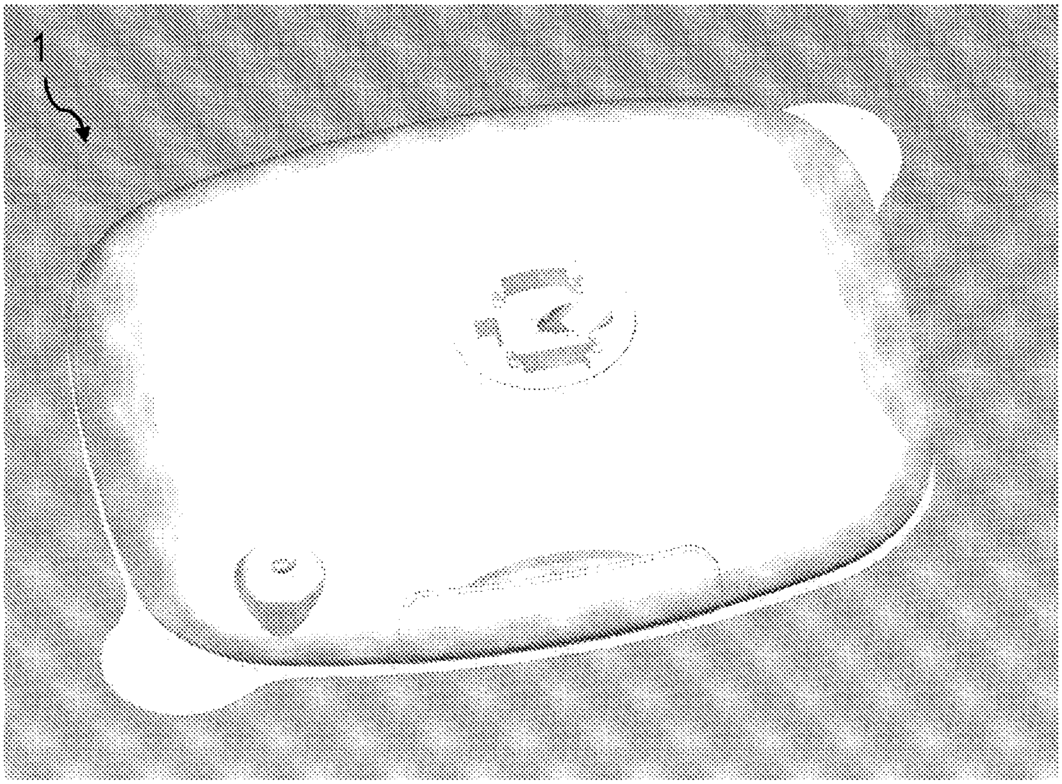
FIG. 3 is a perspective view of one embodiment of an infusion pump.
Figure 4:
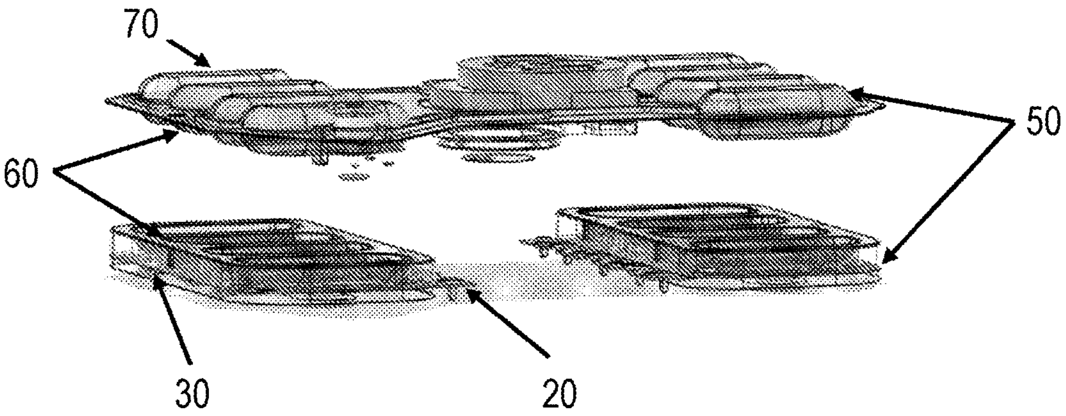
FIG. 4 is a perspective exploded view of one embodiment of an electrochemical actuator included in an infusion pump.

FIG. 3 depicts a perspective view of an infusion pump 1. FIG. 4 shows one embodiment of an internal system of the infusion pump 1. Specifically, in the depicted embodiment, the infusion pump includes one or more arrays of electrochemical actuators including multiple reservoirs 70 and corresponding electrolytic chambers 30. In the depicted arrays, the overall approach is the same: a set of reservoirs 70 and a corresponding set of electrolytic chambers 30 may include corresponding rigid and compliant structures similar to the embodiments described above. However, in some embodiments, it may be advantageous to form multiple reservoirs between a single rigid structure 50, such as a rigid membrane and a corresponding compliant membrane 60 bonded to the rigid membrane. Additionally, multiple electrolytic chambers may be formed in a rigid unitary structure with a single flexible membrane bonded around the openings of the multiple electrolytic chambers to form the desired sealed electrolytic chambers. These structures may be assembled and held proximate to one another to form the overall electrochemical actuators for pumping a substance out of the reservoirs.

In the depicted embodiment, the overall device may include eight separate reservoirs, or any other appropriate number of separate reservoirs, which may either be fluidly connected to a common outlet from the device and/or separate outlets as the disclosure is not so limited. In either case, the depicted construction may simplify the manufacturing of multiple electrochemical actuators using multiple structures formed in the various described rigid and compliant components. Additionally, as elaborated on further below, the rigid membrane, or other structure forming a portion of the reservoirs may include one or more channels, or other hydraulic components, that define the overall layout and functionality of the resulting hydraulic circuit in fluid communication with the individual reservoirs of the electrochemical actuators.

Figure 5:
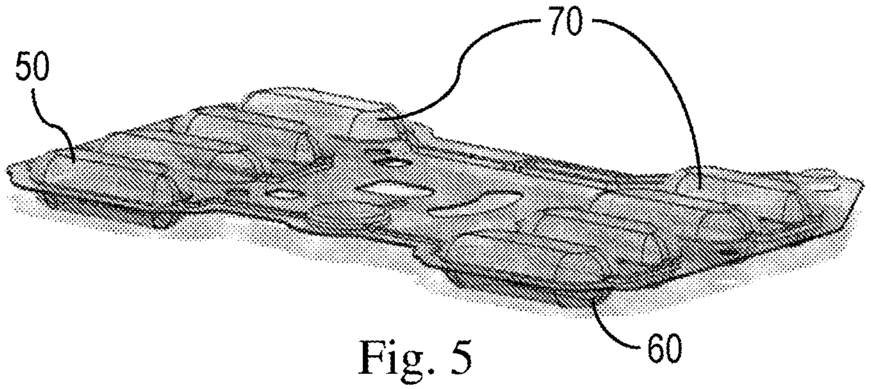
FIG. 5 is a schematic perspective view of one embodiment of a laminated reservoir structure including flow paths formed therein.
Figure 6:
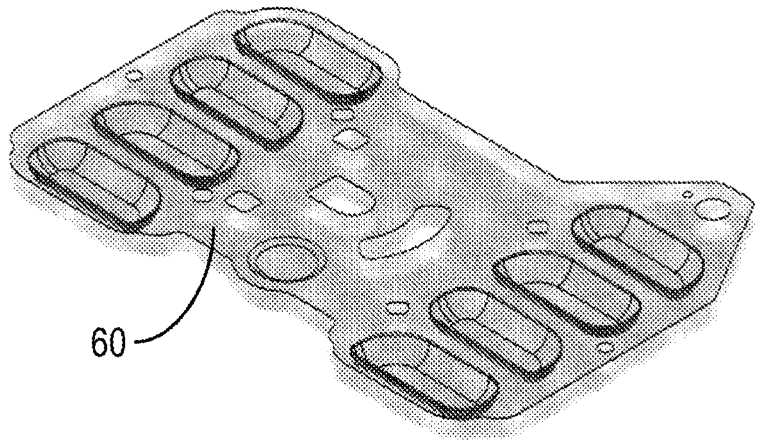
FIG. 6 is a schematic perspective view of a flexible membrane forming a portion of the laminated reservoir structure of FIG. 5.
Figure 7:
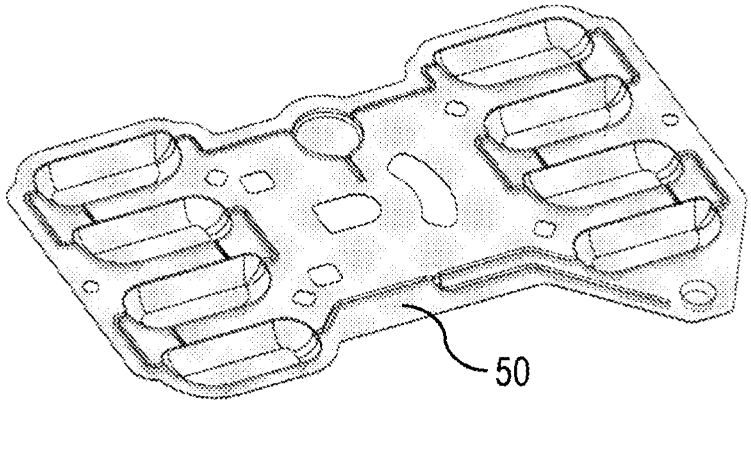
FIG. 7 is a schematic perspective view of a rigid membrane including flow paths formed therein forming a portion of the laminated reservoir structure of FIG. 5.

FIGS. 5-7 depict the construction of one embodiment of an array of reservoirs 70 formed by two laminated membranes. The laminate is made from two thermoformed membranes which are thermally sealed to create a fluid path. In some embodiments, one or more fluid paths are formed from a relatively rigid membrane 50 as shown in FIG. 7 that is more rigid than the flexible membrane 60 shown in FIG. 6 that is disposed against the compliant portions of the corresponding electrolytic chambers to form an array of interconnected electrochemical actuators. The laminate is made from extruded membranes from materials with a desired combination of flexibility, chemical stability, and compatible with the compositions contained within the one or more reservoirs. Once each membrane goes through the thermoforming process, the membranes may be cut to include alignment features and through-holes for inlet and outlet structures. A simple lamination process, akin to that of pill-pack lamination, in which cavities containing offset features of each thermoformed membrane may be used to provide heat and pressure in select areas of the laminate construct.

While a thermoforming process for each membrane is described above, in some embodiments, the rigid portion of the reservoir may be injection molded to form the desired flow paths. During actuation, the flexible actuator layer is deformed to displace a composition out of the reservoirs 70. However, flow paths do not need to move. Accordingly, the other portion of the laminated structure may be thicker, and thus, may be injection molded and/or otherwise formed in a thicker more rigid structure. The thermoformed membrane, or other structure including the flow paths, may be bonded or welded to the compliant membrane to form both the reservoirs 70 and associated one or more flow paths 12.

Figure 8:
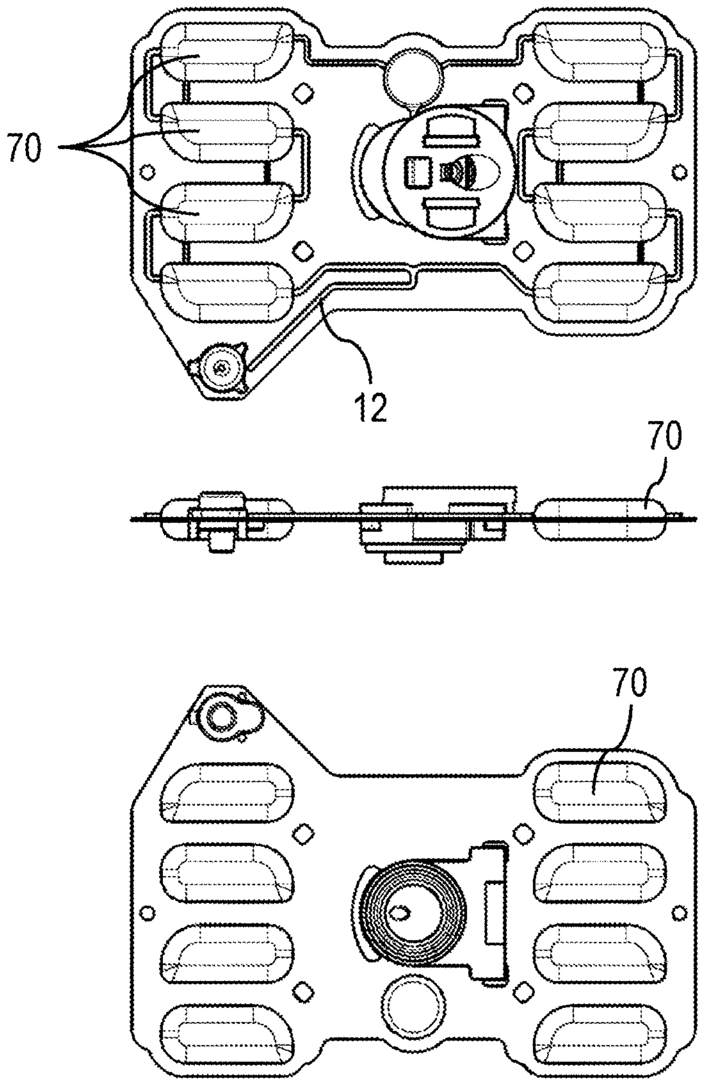
FIG. 8 is one embodiment of a laminated structure forming the reservoirs and flow paths of an infusion pump.
Figure 9:
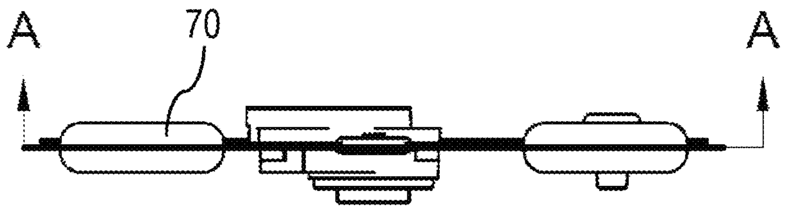
FIG. 9 is one embodiment of a laminated structure forming the reservoirs and flow paths of an infusion pump.
Figure 9A:
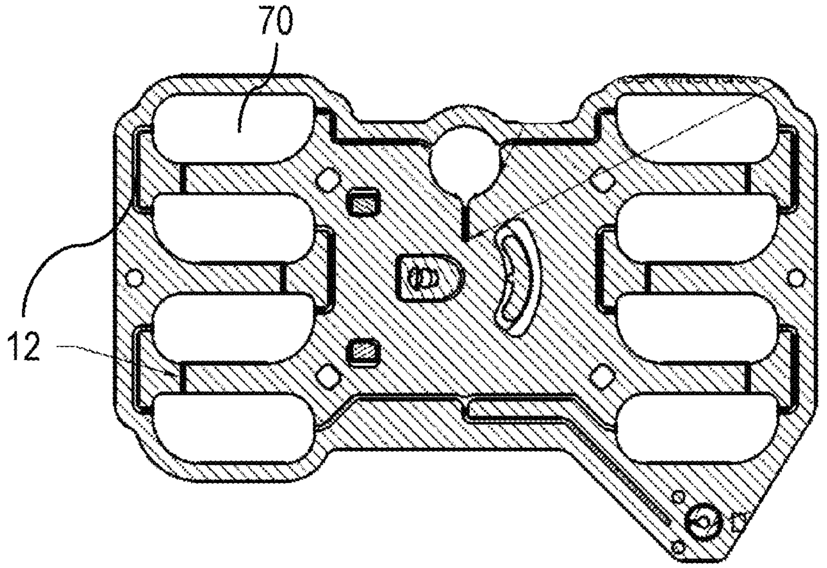
FIG. 9A is a cross-sectional view of the laminated structure of FIG. 9.

Different views of the resulting structure and the associated reservoirs and flow paths are shown in FIGS. 8-9A.

Figure 10:
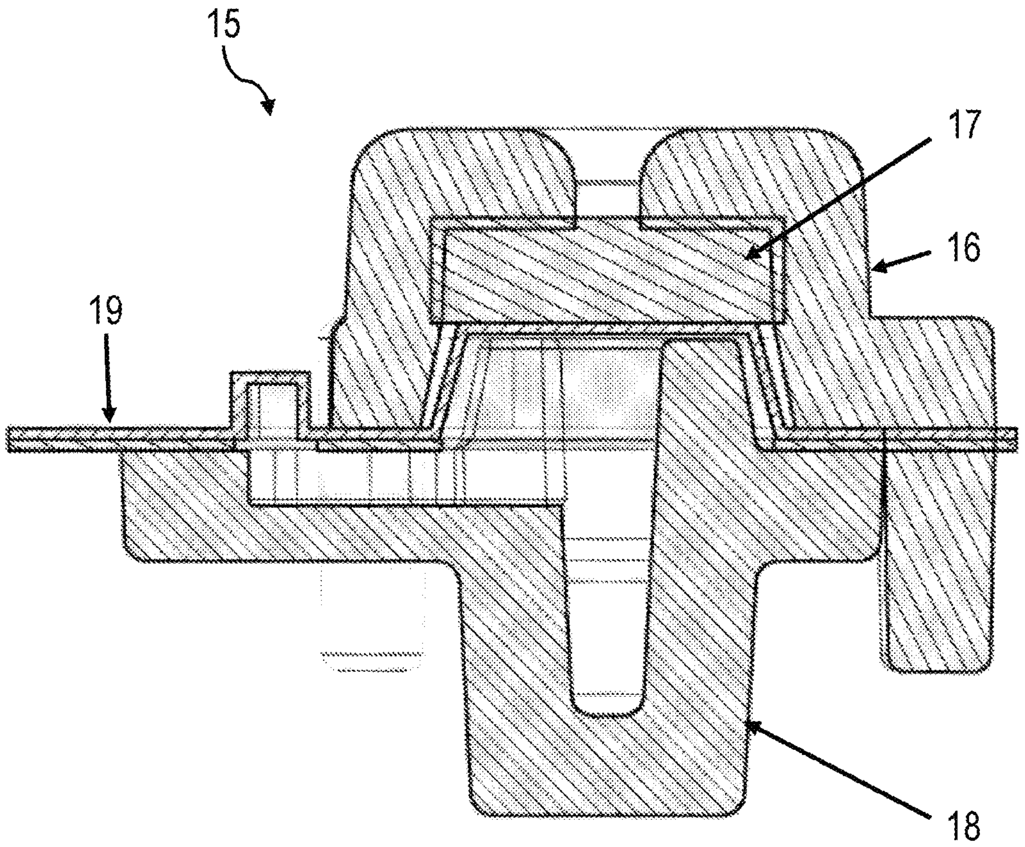
FIG. 10 is a cross-sectional view of one embodiment of an inlet.
Figure 11:
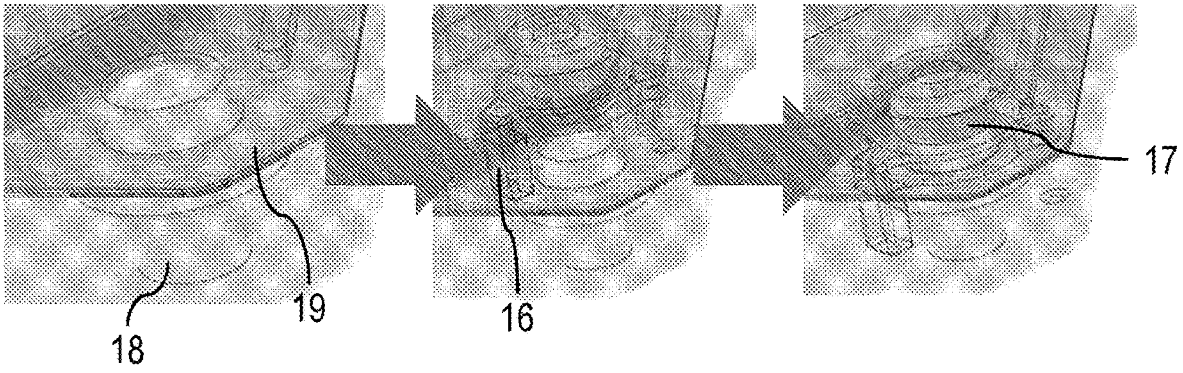
FIG. 11 is a perspective view of an assembly process for an inlet.

FIGS. 10-11 illustrate one embodiment of an inlet 15 that is in fluid communication with the one or more reservoirs of an infusion pump. The inlet may include a receiver 16, a septum 17, and a base 18. The receiver 16 and the base 18 may be rigid components that prevent accidental piercing of the fluid laminates during filling and compressing the septum 17 in order to achieve a seal after filling of the device. Assembly of the inlet may include the steps of: thermally bonding the base 18 to the fluidic laminate 19; press fitting the septum 17 into the receiver 16; and heat-staking or ultrasonically welding the receiver 16 on the assembly. However, it should be understood that other appropriate assembly processes and structures may be used for an inlet in fluid communication with the reservoirs as the disclosure is not so limited.

Figure 12:
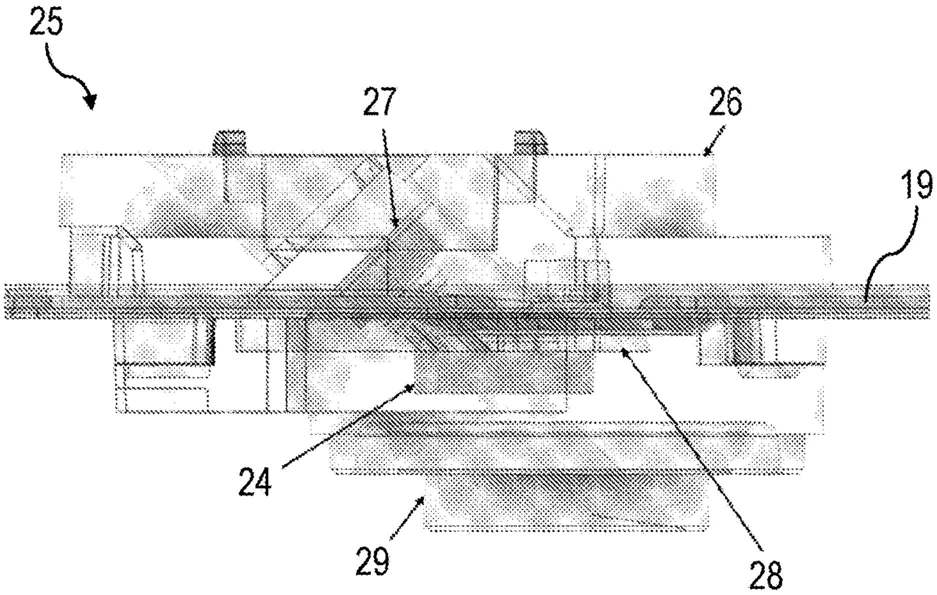
FIG. 12 is a side view of an outlet of an infusion pump formed in a laminated structure.

FIG. 12 depicts one embodiment of an outlet 25 in fluid medication with the plurality of reservoirs of an infusion pump. In the depicted embodiment, the outlet 25 includes five components including: a receiver 26; a receiver septum 27; a distributor 28; a base 29; and a base septum 24. The outlet 25 may be thermally sealed to the microfluidic laminates 19 and mechanically scaled to a cannula during use. Initially, a distributor 28 and base 29 may compress the base septum 24. This compression is made permanent by laminating the distributor 28 and the base 29 to the microfluidic laminates 19. Once the thermal lamination process is completed the receiver septum 24 is placed in the distributor 28 and the receiver 26 is ultrasonically welded to the base 29, which may fix the compression level of the receiver septum 27 and the alignment of the parts of the inserter (including an associated cannula) and the outlet 25. The receiver septum 24 is not intended to be pierced but instead may behave more like an o-ring, or other seal, when pressed against the support column. Thus, in some instances, the receiver septum 24 may be referred to synonymously as a seal in other portions of the current application.

While a particular arrangement for an outlet of an infusion pump associated with a plurality of electrochemical actuators has been described above, it should be understood that any appropriate arrangement for an outlet of the infusion pump may be used as the current disclosure is not limited to any particular construction.

In some instances, an infusion pump may be configured to be filled by a user to permit the infusion pump to be reused and/or deliver any desired combination of therapeutic compounds or other compositions. Thus, in some embodiments, an infusion pump may include flow paths that are configured to accommodate filling by users with relatively high flowrates (≤30 ml/min). To accommodate user filling at these relatively high flowrates, it may be desirable for the reservoirs and flow paths of the device to be configured to facilitate bubble-free filling of the reservoirs and/or filling of the reservoirs while angled with respect to a local direction of gravity. Specific embodiments of structures such as bypass channels and reservoir geometries to enable filling under these conditions are detailed below.

In view of the above, the reservoirs and associated channel and other hydraulic components of a device may be configured to provide a laminar flow of a liquid through the device that minimizes the likelihood of fluid transition into turbulent flow. Thus, the channel inlets into each reservoir may gradually widen to slow down fluid momentum and reduce Reynolds number upon entrance (though higher Reynolds numbers for liquids with larger viscosities than water may also be used). For instance, a Reynolds number may be maintained below 2300 during filling of the reservoirs as the meniscus progresses along the length of each reservoir.

Figure 13A:
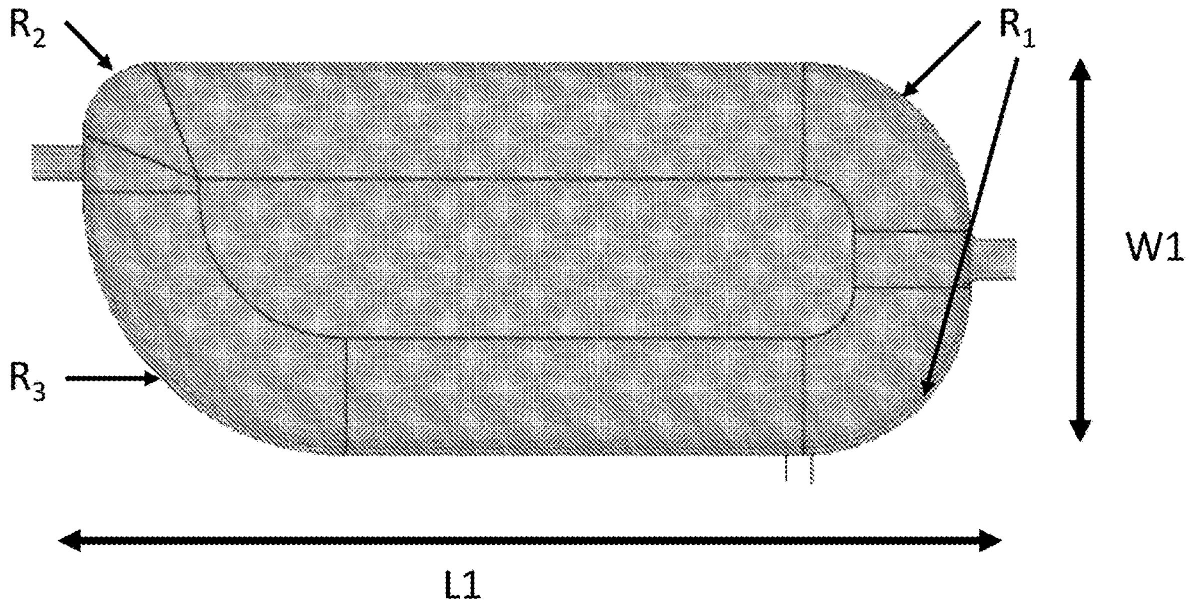
FIGS. 13A-13B depict one embodiment of a reservoir.
Figure 13B:
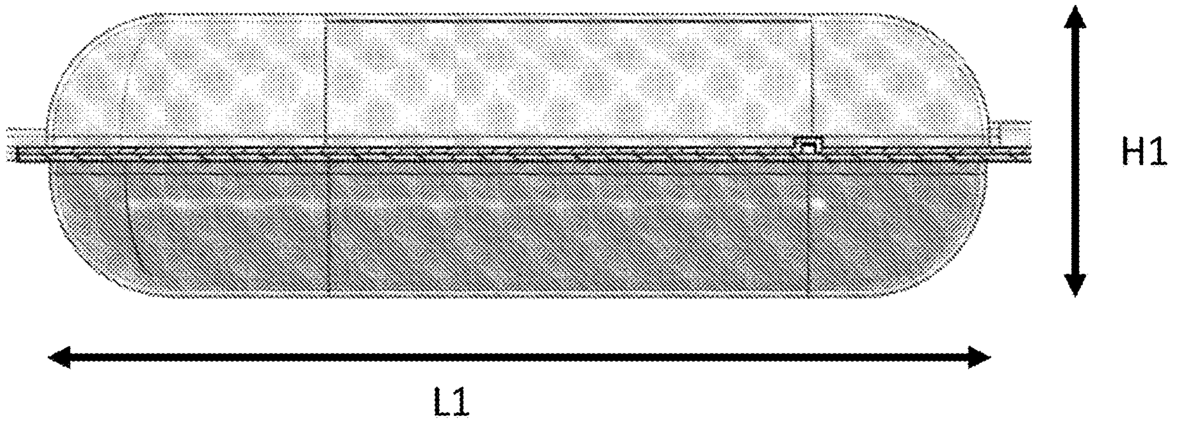

Once fluid enters a reservoir under laminar flow, a significant challenge is to sustain laminar flow and prevent accidental bubble entrapment during filling. Keeping a ratio of Width-to-Height (e.g., see width W1 and height H1 in FIGS. 13A-13B) that approximates 3:2 with a height limit of 5 mm significantly improves bubbleless filling. Additionally, as the meniscus develops inside the reservoir it has been found that fluid may converge asymmetrically due to limits in fabrication, assembly, and/or filling of the reservoirs. Accordingly, in some embodiments, it may be preferable to force an asymmetric velocity vector as the fluid approaches the outlet using an asymmetric shape of the reservoir configured to guide the flow of fluid and resulting meniscus towards an outlet of the reservoir to avoid bubble formation. In some embodiments, this can be achieved by offsetting the outlet channel from the centerline of the width of the channel to the desired side of convergence while sustaining a minimum ratio of the relative radii of curvature of the reservoir adjacent to the outlet (ratio of radii of curvature R3:R2, as depicted in FIG. 13A) greater than or equal to 4:1. However, embodiments in which different ratios of the various geometries are used including ratios both greater than and less than those noted above are also contemplated.

Figure 14:
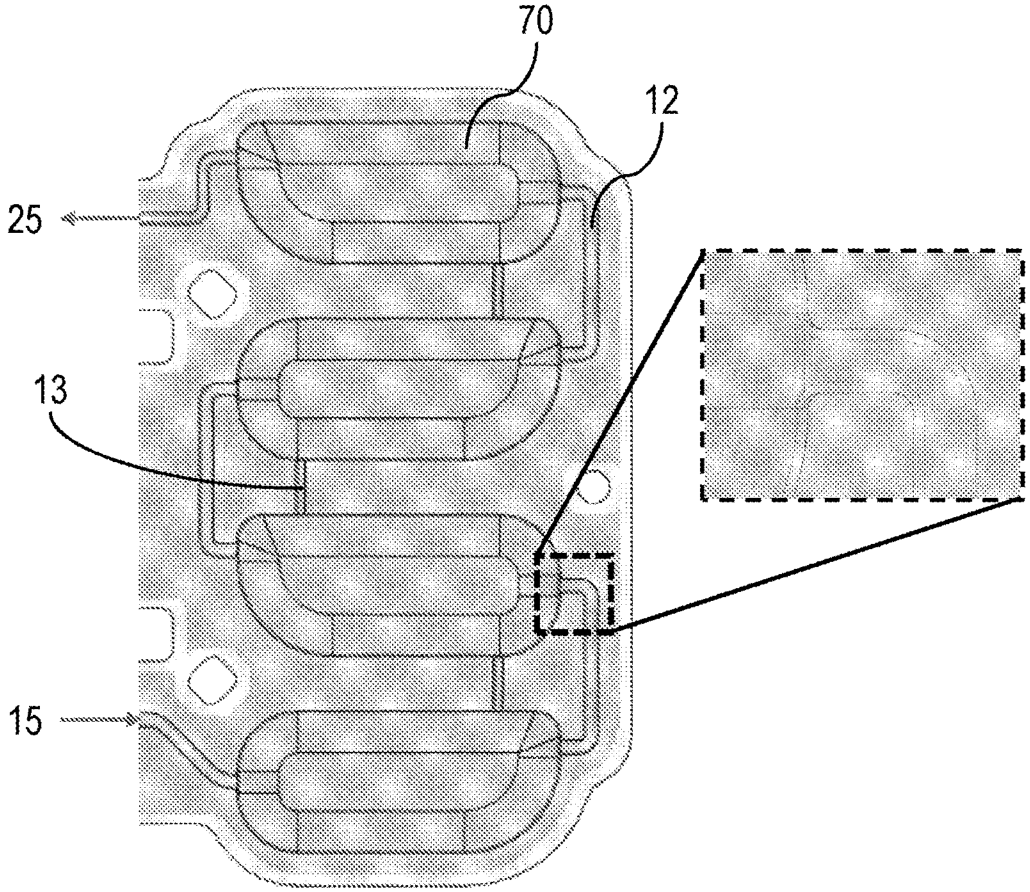
FIG. 14 depicts one embodiment of a flow path including serially connected reservoirs with bypass channels extending between adjacent reservoirs.

FIG. 14 depicts an embodiment of a plurality of serially connected reservoirs 70 with primary channels 12 extending between adjacent upstream and downstream reservoirs. Additionally, the flow paths 12 may include a bypass channel 13 that extends between adjacent upstream and downstream reservoirs such that at least a portion of liquid flowing between the reservoirs may flow through the bypass channel. As elaborated on below, liquid may not flow through the bypass channels below a threshold pressure due to capillary forces within the bypass channels. Correspondingly when a pressure within the reservoirs is above the threshold pressure, such as may occur during a user filling the reservoirs above a threshold filling rate, the liquid may flow through the bypass channels to reduce a flow rate through the primary channels which may help to maintain a desired laminar flow and meniscus formation within the reservoirs during filling.

Figure 15:
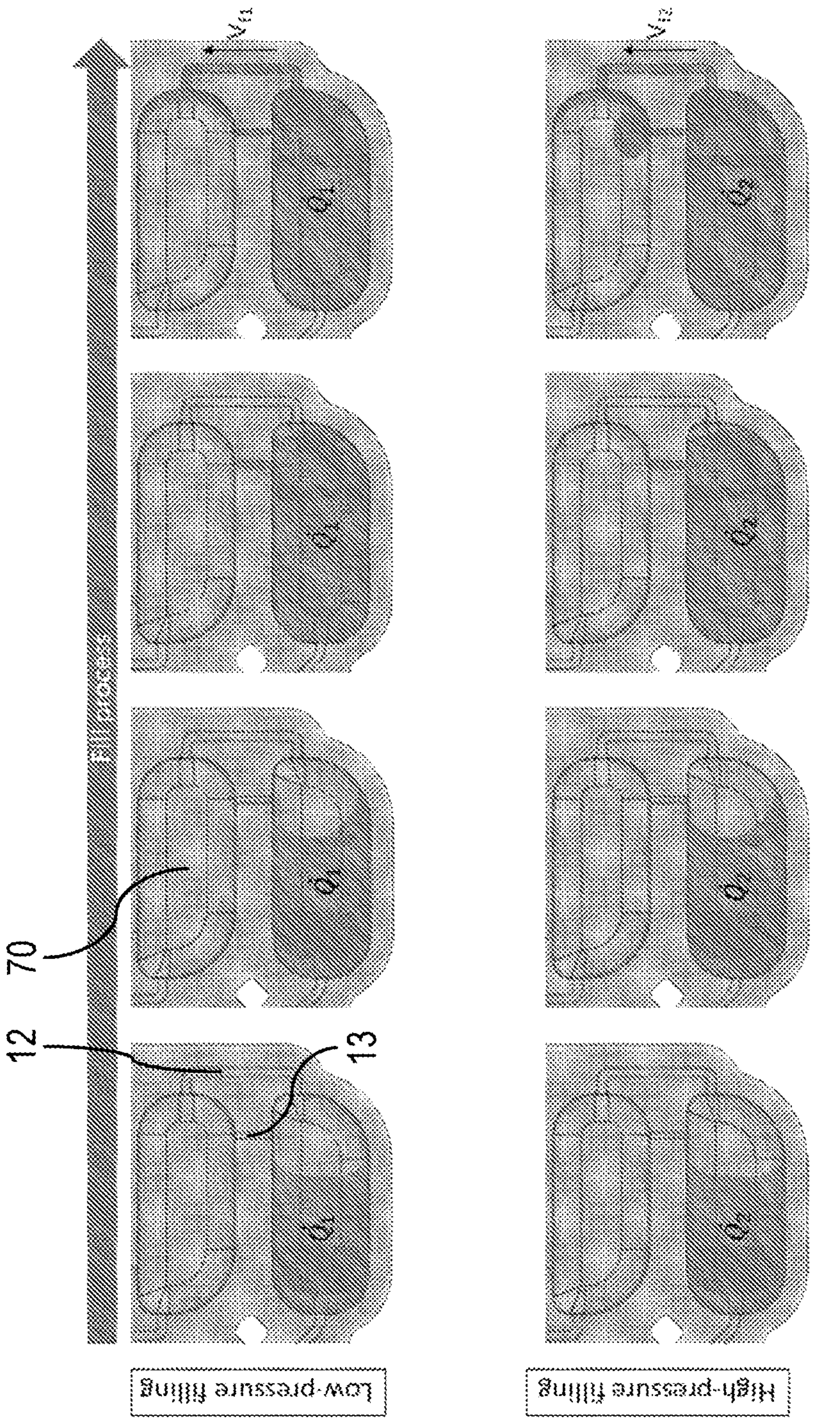
FIG. 15 depicts one embodiment of a filling process of adjacent reservoirs including bypass channels under low-pressure filling and high-pressure filling.

Without wishing to be bound by theory, controlling the meniscus inside each reservoir is strongly dependent on controlling the velocity vector in direction and magnitude. Controlling the magnitude of the velocity vector can be done indirectly by providing a bypass channel 13 that is activated based on a pressure threshold. As can be observed in FIG. 15, a low-pressure filling process will only fill the capillary bypass between two reservoirs 70 in series but without enough pressure to overcome surface tension at the end of the bypass channel 13. Thus, substantially all of the liquid flows through the primary channel 12 to fill the next reservoir 70 in series. In contrast, a high-pressure filling process will result in a higher flowrate ($\dot{Q}_2>\dot{Q}_1$) such that the applied pressure overcomes the surface tension of the liquid at an opening of the bypass channel 13 such that a portion of the liquid will flow through the bypass channel 13 which may substantially reduce a fluid velocity of the fluid flowing through the primary channel 12. This may help to maintain a velocity vector of the fluid flowing through the primary channel 12 to be less than a desired threshold velocity, and in some instances may result in the velocities in each scenario being approximately equal to each other ($V_{f1}\sim V_{f2}$).

Figure 16:
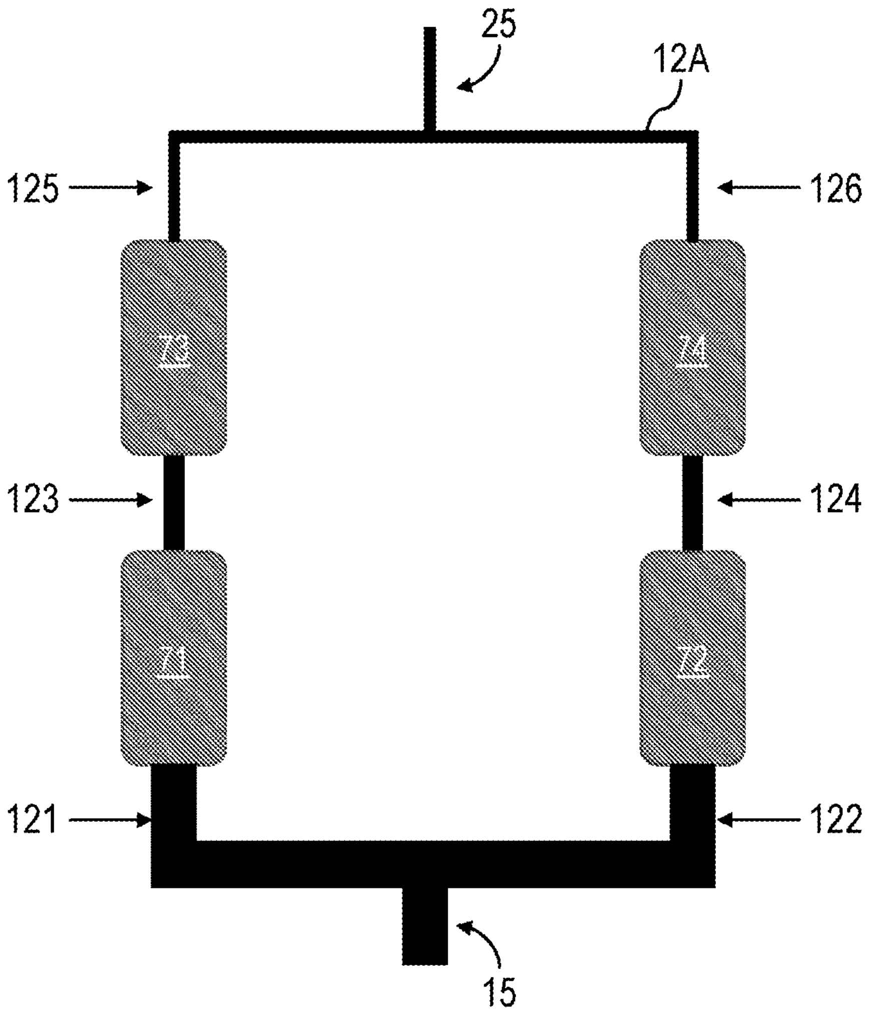
FIG. 16 depicts one embodiment of parallel flow paths including serially connected reservoirs fluidly connected to an associated inlet and outlet of a device.

FIG. 16 depicts one embodiment of two or more sets of serially arranged reservoirs 71-74 connected to an inlet 15 and/or outlet 25 of an infusion pump in series. In embodiments including two or more parallel flows of liquid, it may be desirable to maintain relatively equal flowrates either along a single flow path through the serially arranged reservoirs and/or between the parallel branches during filling and/or pumping of a liquid through the device. For example, in practice, as the fluid path begins to fill during a filling process where an inlet is connected to both parallel flow paths there may be variations and defects in the flow paths that may prevent branches completing filling simultaneously. If this issue compounds downstream then a substantial amount of gas may be entrapped between the convergence point of the parallel branches and the slower meniscus. One approach towards achieving simultaneous filling with minimal bubble formation may be to increase the hydraulic resistance of each flow path in a downstream direction. In the figure, it can be observed how channels connecting two fluid branches containing two reservoirs each include cross-sectional areas that decrease in size in the downstream direction which increases the hydraulic resistance in the downstream direction for each parallel flow path. Corresponding portions of the parallel flow paths may have hydraulic resistances that are approximately equal to one another to provide substantially similar flow properties along each parallel flow path. Due to the increasing hydraulic resistance in the downstream direction, once one reservoir is filled and the meniscus enters a channel with an increased hydraulic resistance, the flowrate of liquid into the other parallel branches that have not filled to the same degree may be accelerated such that the filling of each branch may be automatically adjusted to maintain the filling rate of each branch approximately equal to each other. For instance, if it is assumed that point 121 presents 5% higher hydraulic resistance than point 122 then reservoir 72 will be filled at a higher flowrate. However, once reservoir 72 is filled, hydraulic resistance will increase exponentially for the branch 12A along reservoirs 72 and 74 and flowrate at point 121 will increase dramatically, therefore swiftly minimizing the difference in volume filled between both branches.

Figure 17:
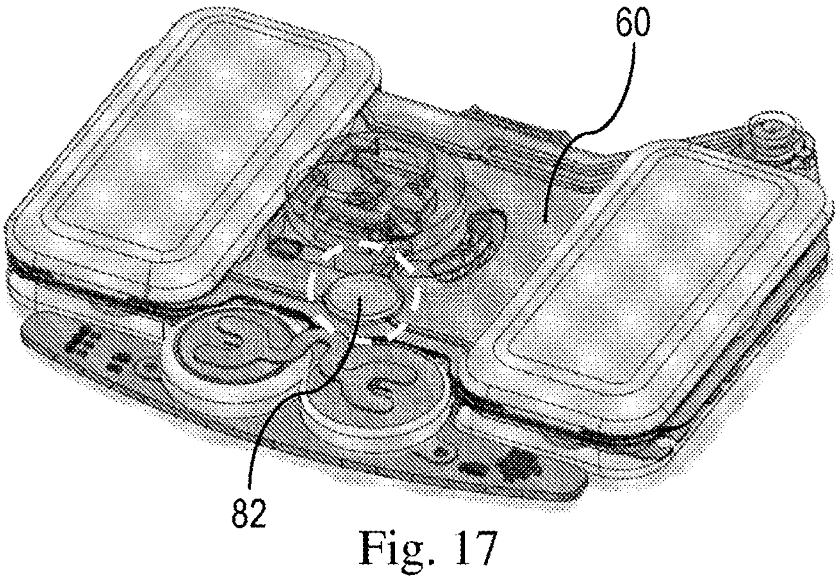
FIG. 17 is a perspective view of one embodiment of an infusion pump including a pressure sensor.
Figure 18:
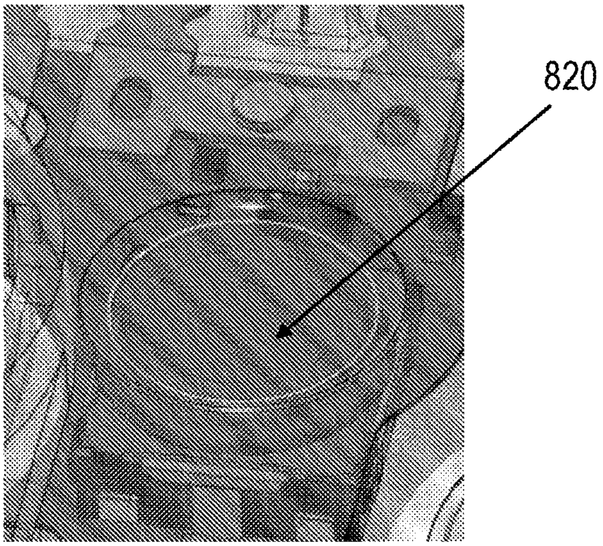
FIG. 18 is a perspective view of an interface area between a compliant membrane and a pressure sensor.
Figure 19:
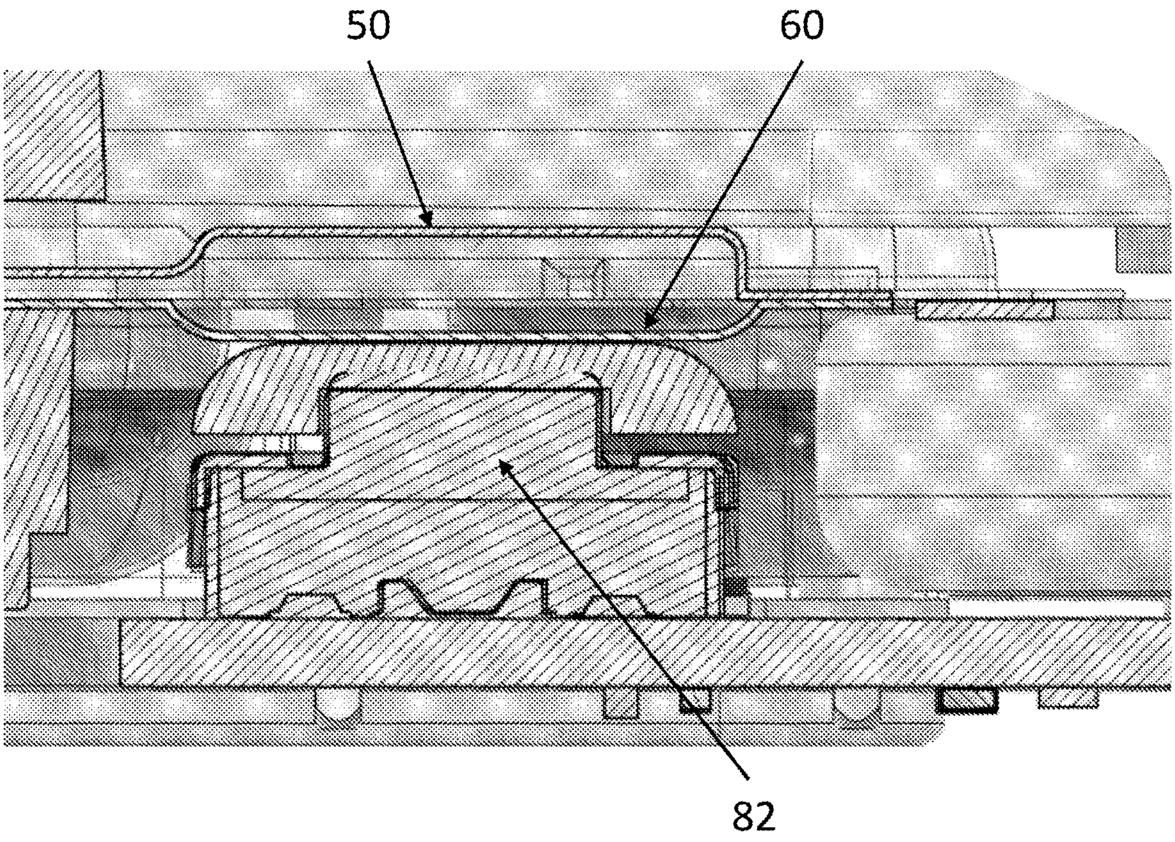
FIG. 19 is a cross-sectional view of an interface area between a pressure chamber formed between a compliant membrane and a rigid membrane or other structure where the pressure chamber is in contact with an associated pressure sensor.

In some embodiments, it may be desirable to include one or more feedback mechanisms to enable dosage confirmation and/or pump status. However, for infusion pumps including laminated structures forming the reservoirs and corresponding flow paths, it may be difficult to interface a circuit and/or sensor with the fluid path in an inexpensive and reliable way. Accordingly, in some embodiments, an interface between the compliant membrane of the fluid path and other electromechanical components such as switches, pressure sensors, strain gauges, light-based distance sensors, among others can be exploited as feedback mechanisms for dose control. For example, as shown in FIGS. 17-19, an infusion pump may include an interface between the compliant layer 60 used to form the reservoirs of the device and a pressure sensor 82 such as a force sensor, strain gauge, force switch, or other appropriate sensor. In one such embodiment, a 0.5 N tactile switch may be used. A corresponding chamber may be formed between the compliant membrane 60 and a corresponding rigid membrane 50, or other structure, such that a desired threshold force to activate the switch, or other sensor for a predetermined operating pressure of the device. During operation, the compliant membrane may press against the sensor. Thus, when an occlusion at the cannula causes pressure to accumulate in the fluid path the force applied to the button or other sensor is directly related to the internal pressure and the area of interface between the button and the compliant membrane. The threshold pressure for actuating a button, or that may be sensed by another appropriate sensor, may be easily modulated by modifying the interface area 820 (as shown in FIG. 18). For a 0.5N device to be triggered at a target occlusion pressure of 30 kPa the interface area may be approximately 4.6 mm in diameter. However, it should be understood that other threshold pressures, interface areas, and/or sensor and chamber constructions may be used as the disclosure is not limited in this fashion.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An infusion pump comprising:

a plurality of serially connected reservoirs of therapeutic fluid, wherein a flow resistance of respective channels that fluidly interconnect adjacent reservoirs and through which the therapeutic fluid flows between adjacent reservoirs of the plurality of serially connected reservoirs increases in a downstream direction from a first reservoir of the plurality of serially connected reservoirs to a last reservoir of the plurality of serially connected reservoirs based on a configuration of each of the respective channels; and an outlet of the infusion pump, wherein the last reservoir of the plurality of serially connected reservoirs is fluidly connected to the outlet for delivering the therapeutic fluid to a subject.

2. The infusion pump of claim 1, wherein the increasing flow resistance to the therapeutic fluid between adjacent reservoirs in the downstream direction is determined by a geometry of the respective channels interconnecting those reservoirs, including at least one of channel length, channel cross-sectional area, or channel cross-sectional shape.

3. The infusion pump of claim 2, wherein each channel of the plurality of channels has an average maximum transverse dimension that is smaller than an average maximum transverse dimension of upstream channels of the plurality of channels.

4. The infusion pump of claim 2, wherein a maximum transverse dimension of each channel of the plurality of channels is between or equal to 0.1 mm and 1 mm.

5. The infusion pump of claim 1, further comprising an outlet channel fluidly connected to the last downstream reservoir and the outlet of the infusion pump.

6. The infusion pump of claim 1, further comprising at least one therapeutic compound disposed in the reservoirs.

7. The infusion pump of claim 1, further comprising at least one pump operatively coupled to at least one of the reservoirs.

8. The infusion pump of claim 7, wherein the at least one pump comprises a plurality of pumps, and wherein each pump is operatively coupled with a separate reservoir of the plurality of serially connected reservoirs.

9. The infusion pump of claim 1, further comprising a filling port fluidly connected to a first upstream reservoir of the plurality of serially connected reservoirs.

10. The infusion pump of claim 1, further comprising filling a first reservoir and second reservoir through a filling port fluidly connected to the first reservoir.

11. The infusion pump of claim 1, wherein a flow resistance between the last downstream reservoir and the outlet is greater than a flow resistance between the last downstream reservoir and an adjacent upstream reservoir of the plurality of reservoirs.

12. An infusion pump comprising:

a first reservoir of therapeutic fluid;

a second reservoir of therapeutic fluid;

a third reservoir of therapeutic fluid;

an outlet of the infusion pump for delivering therapeutic fluid to a subject;

a first channel extending between the first reservoir and the second reservoir and configured to carry the therapeutic fluid between the first reservoir and the second reservoir;

a second channel extending between the second reservoir and the third reservoir and configured to carry the therapeutic fluid between the second reservoir and the third reservoir; and a third channel extending between the third reservoir and the outlet of the infusion pump and configured to carry the therapeutic fluid from the third reservoir to the outlet, wherein a flow resistance of the third channel is greater than a flow resistance of the second channel, and the flow resistance of the second channel is greater than a flow resistance of the first channel due to a difference in at least one of the cross-sectional area, cross-sectional shape, or length of the respective channels.

13. The infusion pump of claim 12, further comprising an outlet channel fluidly connected to the third reservoir and the outlet of the infusion pump.

14. The infusion pump of claim 12, further comprising at least one therapeutic compound disposed in the first, second, and/or third reservoirs.

15. The infusion pump of claim 12, further comprising at least one pump operatively coupled to at least one of the first, second and/or third reservoirs.

16. The infusion pump of claim 15, wherein the at least one pump comprises a plurality of pumps, and wherein each pump is operatively coupled with a separate reservoir of the first, second, and third reservoirs.

17. The infusion pump of claim 12, further comprising a filling port fluidly connected to the first reservoir.

18. A method of operating an infusion pump, the method comprising:

flowing a therapeutic fluid from a first reservoir of the therapeutic fluid that is serially connected to a second reservoir of the therapeutic fluid through a first channel having a first flow resistance, wherein the first channel is configured to carry the therapeutic fluid between the first reservoir and the second reservoir; and flowing the therapeutic fluid from the second reservoir to an outlet of the infusion pump through a second channel having a second flow resistance greater than the first flow resistance, wherein the second channel is configured to carry the therapeutic fluid from the second reservoir to the outlet for delivery to a subject, and the first flow resistance and the second flow resistance are each determined by a cross-sectional geometry of the respective first channel and second channel.

19. The method of claim 18, wherein flowing the therapeutic fluid from the second reservoir includes flowing the therapeutic fluid from the second reservoir to a third reservoir through the second channel and flowing the therapeutic fluid from the third reservoir to the outlet of the infusion pump.

20. The method of claim 19, wherein flowing the therapeutic fluid from the third reservoir to the outlet includes flowing the therapeutic fluid through a third channel having a third flow resistance greater than the second flow resistance, wherein an average maximum transverse dimension of the first channel is greater than an average maximum transverse dimension of the second channel, and an average maximum transverse dimension of the second channel is greater than an average maximum transverse dimension of the third channel.

* * * * *